United States Patent [19]

Ryback

[11] Patent Number: 4,855,512

[45] Date of Patent: Aug. 8, 1989

[54] PREPARATION OF FLUOROPHENOLS

[75] Inventor: George Ryback, Sittingbourne, England

[73] Assignee: Shell Oil Company, Houston, Tex.

[21] Appl. No.: 172,894

[22] Filed: Mar. 25, 1988

[30] Foreign Application Priority Data

Apr. 9, 1987 [GB] United Kingdom ............... 8708517

[51] Int. Cl.$^4$ .............................................. C07C 39/27
[52] U.S. Cl. .................................... 568/775; 568/774
[58] Field of Search ............................... 568/774, 775

[56] References Cited

U.S. PATENT DOCUMENTS 3,043,884  7/1962  Wallenfels et al. ................. 568/775
4,225,731  9/1980  Marhold et al. .................... 568/775
4,508,822  4/1985  Taylor ................................ 435/155

OTHER PUBLICATIONS

Badger, *J. Chem. Soc.* (1949), pp. 2497–2501.
Young et al., *Biochimica et Biophysica Acta* (1969), 177, pp. 381–388.
McCourt et al., *J. Org. Chem.* (1981), 46, pp. 4157–4161.

*Primary Examiner*—Werren B. Lone

[57] ABSTRACT

2- and 3-fluorophenols are prepared by dehydrating 1,2-dihydroxy-3-fluorocyclohexa-3,5-diene under basic conditions and recovering the desired product, for example by fractional distillation.

9 Claims, No Drawings

PREPARATION OF FLUOROPHENOLS

This invention relates to the preparation of fluorophenols.

Fluorinated phenols are useful intermediates in the preparation of, for example, organo-fluorine agrochemicals and pharmaceuticals. However their preparation by conventional chemical methods is comparatively costly and difficult. Thus, for example, 2- and 3-fluorophenol may be prepared from the corresponding commercially available 2- or 3-aminophenol by conversion to and subsequent decomposition of the corresponding diazonium fluoroborates. There is clearly a need for alternative methods of preparing the fluorophenols. There are now available microbiological processes for preparing cyclohexadienes from readily available aromatic starting materials. For example, the preparation of compounds containing a 3-substituted cis-1,2-dihydroxy-cyclohexa-3,5-diene ring from benzene and its derivatives has been described by Taylor (European Pat. No. 0076606) using mutant strains of *Pseudomonas putida*.

The dehydration of cis- and trans-1,2-dihydroxycyclohexa-3,5-dienes in single or multi ring systems has been extensively investigated. Such diols dehydrate readily to phenol by the action of acids and/or heat. The product of dehydration depends on the nature of the other ring substituents present and can be predicted, as demonstrated for example by Badger (J. Chem. Soc., 1949, 2497 to 2501) and also by quantum mechanical calculations. In accordance with these predictions it is to be expected that a compound such as 3-fluoro-1,2-dihydroxy-cyclohexa-3,5-diene will dehydrate to yield predominantly the 2-fluorophenol.

While most investigations carried out have employed acidic conditions, Young et al (Biochimica et Biophysica Acta, 1969, Vol. 177, 381–388) investigated the dehydration of trans 2,3-dihydro-2,3-dihydroxybenzoic acid under both acid and alkaline conditions: in both cases the result was the same, i.e. the product of a major proportion of 3-hydroxybenzoic acid, the expected product in accordance with the predictions mentioned above.

McCourt et al (J. Org. Chem., 1981, Vol. 46, 4157–4161) studied the dehydration of trans-7,8-dihydroxy-7,8-dihydrobenzo[a]pyrene and related polycyclic diols. Dehydration only occurred when a solution of the diol and tetrabutylammonium hydroxide in methanol was evaporated to dryness at 60° C. The dehydration products were unpredictable. They observed no dehydration with tetrabutylammonium hydroxide in other solvents, nor with, for example, potassium hydroxide or potassium methoxide in methanol.

According to the present invention, we provide a process for the preparation of fluorophenols comprising dehydrating 1,2-dihydroxy-3-fluorocyclohexa-3,5-diene in the presence of base and subsequently recovering 3- and/or 2-fluorophenol from the reaction mixture.

Preferably the starting material is cis-1,2-dihydroxy-3-fluorocyclohexa-3,5-diene which has been prepared by the microbial oxidation of fluorobenzene, for example as described in the above mentioned European Pat. No. 0076606, or as described in our European Patent Application Publication No. 0252567.

The fluorophenols may be isolated from the reaction mixture by any suitable standard method, e.g. by acidification and extraction with an organic solvent followed by fractional distillation.

The dehydration is preferably carried out at elevated temperature, suitable temperatures being in the range of 20° to 100° C., preferably 50° to 100° C.

A wide range of basic reagents may be employed for the dehydration, suitably containing HO⁻ or RO⁻ ions (where R is an alkyl or aryl group). Examples are alkaline earth hydroxides in water, alkali metal hydroxides or tetra alkylammonium hydroxides in ionising solvents such as water, alcohols, phenols, dimethylsulphoxide and dimethylformamide. One preferred reagent is aqueous sodium hydroxide, while another is tetrabutyl ammonium hydroxide, employed in aqueous or methanolic solution. Other preferred basic reagents include other alkali metal or alkaline earth hydroxides, such as lithium hydroxide, sodium hydroxide, potassium hydroxide and barium hydroxide. Alternative basic reagents include potassium t-butoxide.

A preferred reaction medium is water but other polar solvents may be employed such as alcohols, e.g. methanol, ethanol, isopropanol and t-butanol, and dimethylformimide and dimethyl sulphoxide, and mixtures thereof.

It is preferred to use an excess of base and a preferred molar ratio of base to fluorodiene-diol starting material ranges from 1:1 to 60:1 dependent on the basic reagent used.

We have surprisingly found that, using the process of the invention, the dehydration proceeds to yield substantial quantities of 3-fluorophenol together with 2-fluorophenol. Thus for example, when using tetrabutyl ammonium hydroxide as basic reagent, almost complete dehydration of diene diol occurred to give a mixed product containing approximately 30% 3-fluorophenol. This unexpected increase in the yield of 3-fluorocatechol in the presence of base is all the more surprising in that, under acid conditions the predictable dehydration to a predominantly 2-fluorophenol product occurs with the presence of only trace quantities of 3-fluorophenol.

The following examples are given to illustrate the invention.

EXAMPLE 1

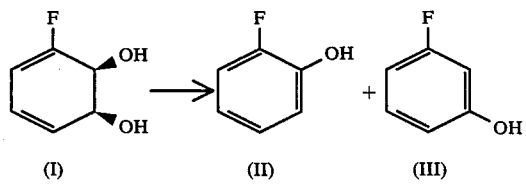

(I)   (II)   (III)

Cis-1,2-dihydroxy-3-fluorocyclohexa-3,5-diene (I) was dehydrated with a number of different basic reagents as listed in Table 1. The concentrations of the reagent and diene (I), the solvent used and the reaction conditions (i.e. temperature and time) are given in Table 1. In each case the total volume of reaction mixture was 2 ml.

The presence of unreacted diene (I) and the dehydration products 2-fluorophenol (II) and 3-fluorophenol (III) was analysed by high performance liquid chromatography (HPLC) after dilution with water. HPLC analyses were performed using a Spherisorb S5C6 column (15 cm×4.6 mm) eluted with 20:80 (v/v) methanol-water containing 0.1% (v/v) acetic acid. Detection was by uv-monitor at 220 nm.

For comparison purposes, three runs (Runs 9, 10 and 11) were included using acidic dehydration conditions. Each dehydration gave very high conversion to 2-fluorophenol (II) in accordance with theoretical predictions, with very low yield of 3-fluorophenol (III).

jacketed Vigreux column. The first fraction (2.37 g) comprised 11% 3-fluorophenol; the second fraction (2.77 g) comprised 36% 3-fluorophenol; and the third fraction (4.25 g) comprised 95% 3-fluorophenol.

TABLE 1

| Run No. | Reaction Conditions | | | | Initial Molar Concentration | | Residual Diene (I) (Molar %) | Products Yield of (II) + (III) (Molar %) | Molar Ratio (II):(III) |
|---|---|---|---|---|---|---|---|---|---|
| | Reagent | Solvent | Temp. °C. | Time | Reagent | Diene (I) | | | |
| 1 | LiOH | H$_2$O | 100 | 35 min | 2.5 | 0.09 | 0 | 91 | 2.69 |
| 2 | NaOH | H$_2$O | 0 | 48 hr | 5.0 | 0.09 | 88 | 12 | 3.24 |
| 3 | NaOH | H$_2$O | 70 | 15 min | 5.0 | 0.09 | 0 | 94 | 2.93 |
| 4 | KOH | H$_2$O | 100 | 20 min | 5.0 | 0.09 | 0 | 94 | 2.87 |
| 5 | Ba(OH)$_2$ | H$_2$O | 100 | 30 min | 0.1 | 0.09 | 0 | 90 | 2.81 |
| 6 | Bu$_4$NOH | H$_2$O | 100 | 45 min | 1.0 | 0.09 | 0 | 96 | 2.36 |
| 7 | Bu$_4$NOH | MeOH | 65 | 45 min | 1.0 | 0.02 | <5 | 70 | 2.82 |
| 8 | KOBu$^t$ | Bu$^t$OH | 100 | 5 min | 0.06 | 0.04 | 15 | 59 | 5.5 |
| 9 | HCl | H$_2$O | 20 | 1 hr | 0.5 | 0.2 | 30 | 68 | 60 |
| 10 | HCl | H$_2$O | 20 | 18 hr | 0.5 | 0.2 | 0 | 92 | 56 |
| 11 | H$_2$SO$_4$ | MeOH | 65 | 5 min | 0.5 | 0.04 | 0 | 86 | >30 |

EXAMPLE 2

1,2-dihydroxy-3-fluorocyclohexa-3,5-diene (I) (1.18 g), 10M aqueous NaOH (5 ml) and water (45 ml) were heated at 100° C. for 15 minutes. HPLC analysis indicated complete conversion of the diene to 2- and 3-fluorophenol in the ratio 2.67:1 (total yield 97%). The cooled dark-brown solution was adjusted to pH 6 with hydrochloric acid and extracted with three portions of diethyl ether. HPLC analysis showed that 2-fluorophenol (5.5% of the original amount) and traces of 3-fluorophenol remained in the aqueous solution. The ether extract was dried over NaSO$_4$ and evaporated. The residue (0.96 g) (whose infrared spectrum showed no absorption peaks other than those due to 2- and 3-fluorophenol) was redistilled under reduced pressure (70 torr; bath 100°–120° C.) to give a colourless liquid (0.85 g; 84% yield). The ratio of 2-fluorophenol (II) to 3-fluorophenol (III) in the product was 2.36:1 as measured by HPLC.

Separation of 2-Fluorophenol (II) and 3-Fluorophenol (III)

This can be readily accomplished by fractional distillation, the boiling point of 2-fluorophenol being 152° C. and that of 3-fluorophenol being 178° C.

Thus in a small scale experiment, 10.75 g of a mixture comprising 2-fluorophenol 4.18 g (39%) and 3-fluorophenol 6.57 g (61%) was subjected to fractional distillation at a pressure of 70 mm Hg using a 15 cm vacuum

I claim:

1. A process for the preparation of fluorophenols comprising dehydrating 1,2-dihydroxy-3-fluorocyclohexa-3,5-diene in the presence of a base containing HO$^-$ or RO$^-$ ions in which R is an alkyl or aryl group at about 20° C. to about 100° C.

2. A process according to claim 1 wherein the starting material is cis-1,2-dihydroxy-3-fluorocyclohexa-3,5-diene.

3. A process according to claim 2 wherein the cis-diene has been prepared by the microbial oxidation of fluorobenzene.

4. A process according to claim 1, 2 or 3 wherein 3-fluorophenol is recovered from the reaction mixture.

5. A process according to claim 4 wherein the 3-fluorophenol is recovered by acidification of the reaction mixture and extraction with an organic solvent followed by fractional distillation.

6. A process according to claim 1 wherein the base is selected from alkali metal hydroxides, alkaline earth hydroxides and tetraalkylammonium hydroxides.

7. A process according to claim 6 wherein the base is selected from aqueous sodium or potassium hydroxide and aqueous or methanolic tetrabutyl ammonium hydroxide.

8. A process according to claim 1 wherein the temperature is in the range of from 50° to 100° C.

9. A process according to claim 1 wherein the dehydration is carried out in the presence of an excess of base.

* * * * *